United States Patent
Swanger et al.

(10) Patent No.: US 7,570,794 B2
(45) Date of Patent: Aug. 4, 2009

(54) SYSTEM AND METHOD FOR EVALUATING A MACHINED SURFACE OF A CAST METAL COMPONENT

(75) Inventors: Michael E. Swanger, Shelby Township, MI (US); John S. Agapiou, Rochester Hills, MI (US); Robert J. Hogarth, Millington, MI (US)

(73) Assignee: GM Global Technology Operations, Inc., Detriot, MI (US)

( * ) Notice: Subject to any disclaimer, the term of this patent is extended or adjusted under 35 U.S.C. 154(b) by 601 days.

(21) Appl. No.: 11/219,043

(22) Filed: Sep. 2, 2005

(65) Prior Publication Data

US 2007/0052795 A1 Mar. 8, 2007

(51) Int. Cl.
  *G06K 9/00* (2006.01)
  *G06K 9/68* (2006.01)
  *G06K 9/60* (2006.01)
  *H04N 9/47* (2006.01)

(52) U.S. Cl. .................. 382/141; 382/108; 382/194; 382/218; 382/308; 348/86; 348/92; 348/128

(58) Field of Classification Search ............... 382/151, 382/222, 225, 194–196, 298, 308, 100, 108–109, 382/141–152, 216–219; 348/86, 88, 90, 348/92, 125–128

See application file for complete search history.

(56) References Cited

U.S. PATENT DOCUMENTS

| | | | | |
|---|---|---|---|---|
| 4,519,041 A | * | 5/1985 | Fant et al. | 382/141 |
| 4,555,798 A | * | 11/1985 | Broadbent et al. | 382/144 |
| 4,616,603 A | * | 10/1986 | Kubis et al. | 123/41.84 |
| 4,845,558 A | * | 7/1989 | Tsai et al. | 348/126 |
| 4,926,452 A | * | 5/1990 | Baker et al. | 378/22 |
| 5,081,656 A | * | 1/1992 | Baker et al. | 348/87 |
| 5,850,466 A | * | 12/1998 | Schott | 382/141 |
| 6,157,736 A | * | 12/2000 | Jodoin et al. | 382/173 |
| 6,839,457 B1 | * | 1/2005 | Azuma et al. | 382/131 |
| 2002/0088952 A1 | * | 7/2002 | Rao et al. | 250/559.45 |
| 2005/0220335 A1 | * | 10/2005 | Budd | 382/152 |

* cited by examiner

*Primary Examiner*—Daniel G Mariam
*Assistant Examiner*—Manav Seth (57) ABSTRACT

A method and system are provided for non-contact evaluation of a machined surface of a cast-metal part, including a vision-based porosity inspection station. A digital image of the machined surface is acquired, oriented and scaled to an XY coordinate system, filtered, and inverted. A second image is generated with known design surface features eliminated. Each pixel of the inverted digital image is XOR-compared with a corresponding pixel of the second image. Identified common surface features common to both images is analyzed statistically for conformance to a threshold. A defect is identified as any identified surface feature common to both images which exceeds the threshold. The system moves the part for further processing if a statistical analysis of defects indicates an acceptable component, and alternatively, removes the part from further processing if the analysis indicates a flawed component.

17 Claims, 4 Drawing Sheets

SYSTEM AND METHOD FOR EVALUATING A MACHINED SURFACE OF A CAST METAL COMPONENT

TECHNICAL FIELD

This invention pertains generally to cast-metal parts and vision-based, non-contact inspection systems for inspecting cast-metal parts.

BACKGROUND OF THE INVENTION

Manufacturers of cast-metal components having machined surfaces typically inspect each component to identify presence of surface defects, to determine if the component is in compliance with quality standards. Surface defects of interest typically include pores, or openings, which indicate voids in the cast metal. Such voids are caused, for example, by impurities in the cast metal, and metal flow problems during the casting process. A specific pore may indicate a small void, or it may indicate and lead to a much larger void below the surface. A pore may be located in a critical location in the cast part, such as an edge of a casting, or near a heat-affected zone, and affect overall part quality and performance in-use. Alternatively, a pore may be located in a non-critical location, with little or no effect on part quality and in-use reliability and performance. Voids in the casting typically associated with surface defects include, by way of example, a small isolated opening, a pore with a concave region, a convex hull in the casting created prior to pore separation, a top edge-connected pore, or, an edge-connected pore on the inside of a concave region.

One present method and apparatus for inspecting and detecting surface defects comprises having a human operator measure a machined surface using a MYLAR™ (or equivalent) template, and visually evaluating the result to identify and detect defects therefrom. The quality and reliability of such inspection is subject to the operator's overall capability and performance over time.

A second method and system as been developed comprising a surface porosity inspection process using a line-scan camera and lighting system to obtain an image of a surface. Software was developed to evaluate surface pores using adaptive threshold and characterization of isolated and edge-connected pores. An adaptive threshold grayscale process generates a black and white image of the surface. An inverted binary (i.e. pure black and white) image is presented for processing to identify the pores using algorithms. Such a system is not robust in a manufacturing production environment because of limitations related to identification of surface defects with edge-connected pores. These limitations included an inability to reliably detect a pore with a concave region, a convex hull created prior to pore separation, or an edge-connected pore on an inside of a concave region. In addition, size of convexity defects and neighboring pores may be inaccurately measured, leading to false detections. Furthermore, the system may falsely detect small defects, or sharp features, or tightly-cornered features. Such a system typically requires an operator to inspect and sort parts after machine inspection in conjunction with the analysis from the inspection system, defeating the purpose of the inspection station, and introducing risk of human error into the process.

Therefore, there is a need to objectively inspect and analyze a surface of a machined, cast-metal part at manufacturing line processing rates to accurately, repeatably, and reliably identify defects so as to minimize and eliminate false-pass errors. There is a further need to reliably identify intricately-shaped defects and high-density small-sized defects. There is a further need to minimize operator involvement in the inspection process, and improve part throughput rate of the inspection process.

SUMMARY OF THE INVENTION

In accordance with the present invention, a method and system provides a computer-based visual, non-contact, inspection of machined surfaces of cast metal parts, to reliably identify and detect surface defects, according to predetermined quality specifications. The disclosed method and system operates at production line rates. The method and system provide a vision-based system to identify and evaluate specific casting defects generally known as pores, and eliminate a need for close operator attendance and interaction that previously has been required to visually inspect critical machined surfaces of certain components, for example cast engine components. The method and system reduce part evaluation time, improve product reliability, and provide greater consistency of part evaluation while eliminating potentially arbitrary decision-making by an operator regarding surface quality that may occur in a production environment. In general, all parts are evaluated using the same measurement system and evaluation criteria, and unacceptable parts are automatically removed from the manufacturing line.

The present method and system for evaluating a machined surface of a cast-metal part preferably comprises a plurality of conveyors, operable to move the cast-metal part to and from a porosity inspection station. The porosity inspection station comprises a digital monochrome camera, a lighting station, and a precision-controlled transfer station. There is a computer workstation, having a plurality of data processing computers, and a graphical user interface. The workstation is operably connected to the plurality of conveyors, and signally and operably connected to the porosity inspection station.

In accordance with the present invention, the system and method are operable to acquire an original pixelated image of the machined surface, wherein each pixel comprises a digitized representation of a portion of the machined surface, and identify known design surface features in the original pixelated image, based upon predetermined criteria. The original pixelated image of the machined surface is oriented and scaled to an XY coordinate system, based upon the known design surface features. An inverted digital image of the machined surface is generated. A second image of the machined surface is generated, comprising eliminating the known design surface features from the inverted digital image. Each pixel of the inverted digital image is compared with a correspondingly located pixel of the second image, with pixel location based upon the pixelated image oriented and scaled to the XY coordinate system. Any surface feature common to the inverted digital image and the second image is identified. Each identified surface feature common to both images is analyzed statistically for conformance to a threshold. A defect is identified as any identified surface feature common to both images which exceeds the threshold.

Another aspect of the invention comprises the computer workstation operable to control the plurality of conveyors to move the cast-metal component into position for further processing when a quantity of identified defects is below a threshold. The computer workstation is operable to control the plurality of conveyors to move the cast-metal component out of position for further processing when the quantity of identified defects exceeds the threshold.

It is a further aspect of the present invention to provide the method and system with a decision scheme in which only parts meeting the predetermined quality specifications are accepted for further processing.

It is a further aspect of the present invention to provide the method and system with a scheme to determine density of surface defects within a specified region of interest.

It is an aspect of the present invention to identify surface defects with: a concave region, and, when a convex hull is created prior to defect (pore) separation, a top edge-connected pore, an isolated pore, and, an edge-connected pore on an inside portion of a concave region, It is also an aspect of the present invention to analyze a pore and defect in relationship to neighboring defects and sharp or tight cornered features.

These and other aspects of the invention will become apparent to those skilled in the art upon reading and understanding the following detailed description of the embodiments.

BRIEF DESCRIPTION OF THE DRAWINGS

The invention may take physical form in certain parts and arrangement of parts, the embodiment of which will be described in detail and illustrated in the accompanying drawings which form a part hereof, and wherein.

DETAILED DESCRIPTION OF THE PREFERRED EMBODIMENT

Figure 1:
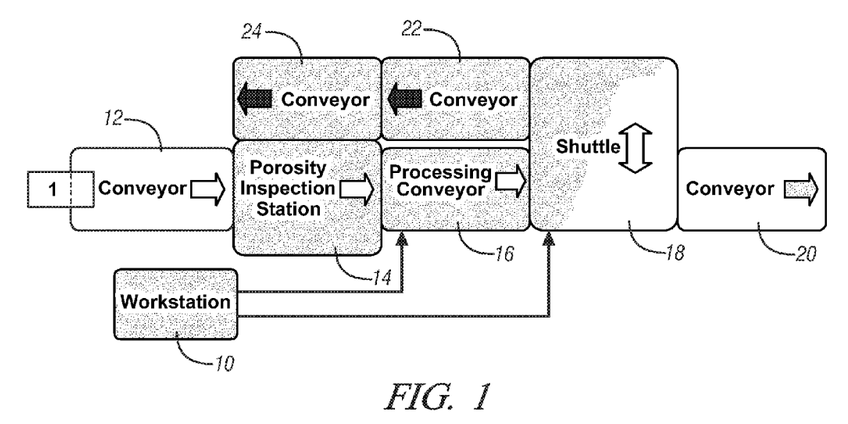
FIG. 1 is a plan-view schematic diagram of an exemplary inspection system, in accordance with the present invention.
Figure 2:
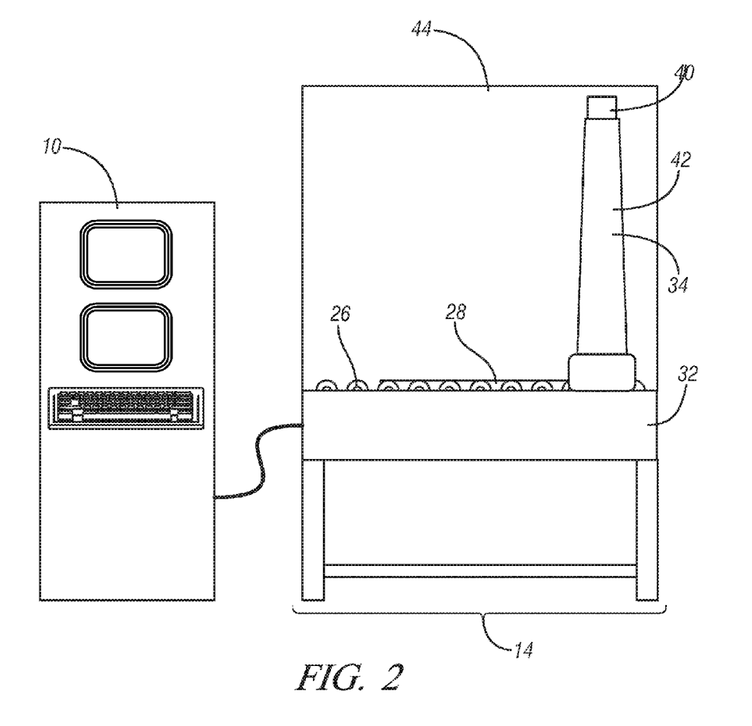
FIG. 2 is a front-view schematic diagram of an element of the exemplary inspection system, in accordance with the present invention.
Figure 3:
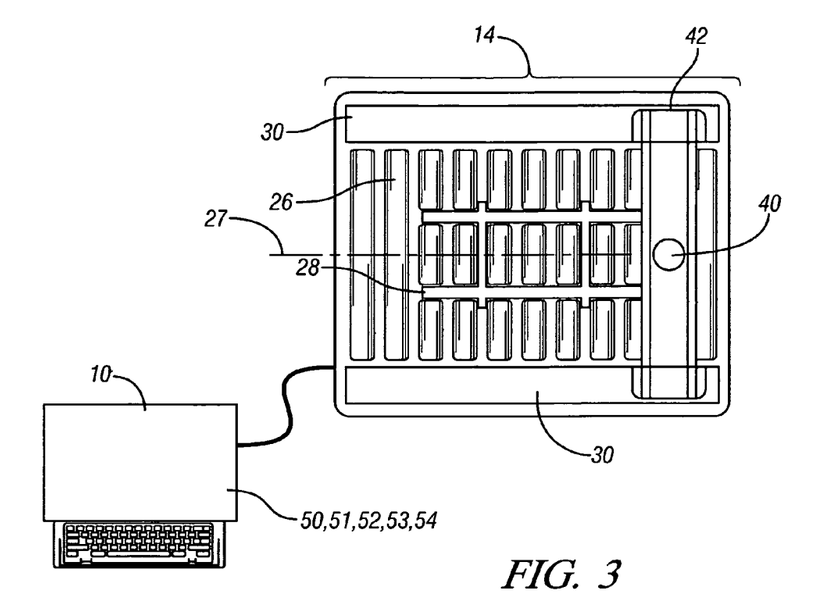
FIG. 3 is a plan-view schematic diagram of an element of the exemplary inspection system, in accordance with the present invention.
Figure 4:
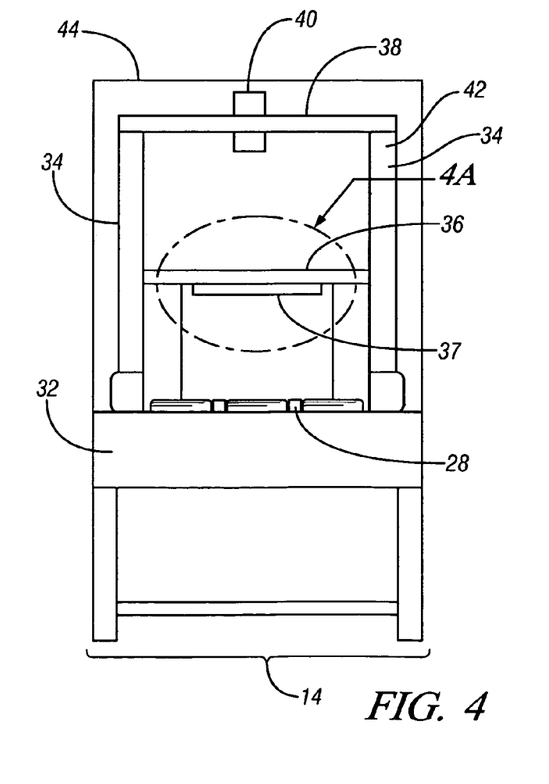
FIG. 4 is a side-view schematic diagram of an element of the exemplary inspection system, in accordance with the present invention.
Figure 4A:
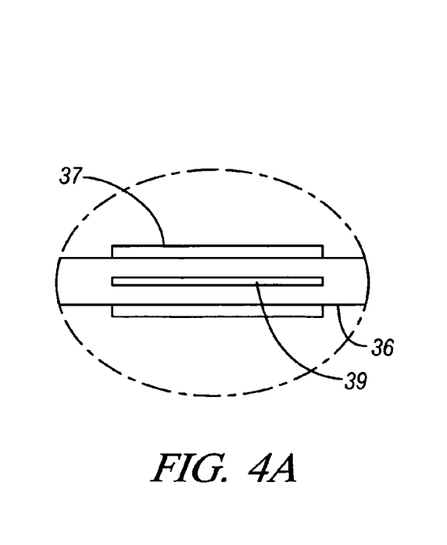
FIG. 4A is a detailed plan-view schematic diagram of an element of the exemplary inspection system, in accordance with the present invention.

Referring now to the drawings, wherein the showings are for the purpose of illustrating the invention only and not for the purpose of limiting the same, FIG. 1 shows a schematic diagram of an exemplary vision system which has been constructed in accordance with an embodiment of the present invention. The exemplary vision system comprises a feed conveyor 12, porosity inspection station 14, processing conveyor 16, part shuttle 18, production conveyor 20, and scrap conveyors 22, 24. Each of the aforementioned devices is operably controlled by the workstation 10, as described in detail hereinafter. In overall operation, a component 1 for inspection is presented to the feed conveyor 12, preferably at a production line rate. An exemplary line rate is preferably in the range of twenty seconds per component evaluated, whereas the actual process of acquiring an image of the surface of the component 1 takes approximately five to seven seconds. When the porosity inspection station 14 is prepared to receive and inspect the component 1, the workstation 10 controls feed conveyor 12 to move the component 1 into the porosity inspection station 14. The component 1 is moved thereto, and inspected, as described herein. When the inspection is complete, the workstation 10 controls the processing conveyor 16 to move the component to part shuttle 18. When the workstation 10 determines the component 1 is acceptable, i.e. contains insufficient defects to warrant scrap or rework, the shuffle 18 moves the component to the production conveyor 20 for further processing. When the workstation 10 determines the component 1 is unacceptable, i.e. contains sufficient defects requiring the component 1 to be scrapped or reworked, the shuttle 18 moves the component to the scrap conveyors 22, 24. The exemplary component 1 of this embodiment comprises a cast-aluminum block for an internal combustion engine having multiple cylinders.

Referring now to FIGS. 2-4A, front-view, plan-view, and side-view schematic diagrams of the porosity inspection station 14 with the workstation 10 of the exemplary inspection system are described in detail. The porosity inspection station 14 includes a base 32, having a roller conveyor 26 and a part elevator and inspection surface 28, and an inspection station 42 comprising a two-tiered camera/lighting scanning mast arrangement. The base 32 has conventional roller conveyor 26 operable to move component 1 into position, wherein the component is elevated onto the inspection surface 28 for inspection. The component 1 is preferably placed on the inspection surface 28 in a substantially correct position and orientation using the roller conveyor 26 and the part elevator, including a part placement sensor (not shown), with the machined surface of interest for inspection suitably positioned for viewing by the two-tiered camera/lighting scanning mast arrangement 42. This is preferably accomplished using known conveying and positioning systems. A skilled practitioner is able to correctly place and orient a series of components in a predetermined location for inspection. The workstation 10 is operable to detect that each component 1 is in correction position for inspection, prior to executing any inspection algorithm. The base 32 includes a pair of bearing tracks 30, each track 30 running parallel to an axis 27 longitudinal to flow of components through the system 14. Inspection system 42 includes a precision-controlled transfer station, operable to tram the two-tiered camera/lighting scanning mast arrangement on the bearing tracks 30 and over the component 1 for inspection. Inspection system 42 comprises a pair of a support masts 34, an upper tier 38 for mounting a camera 40, and a lower tier 36 for mounting a lighting system 37, and has an enclosure 44 to visually enclose and shield at least a portion of the component from ambient light, to facilitate the vision inspection process. The support masts 34 comprise a pair of vertical support legs orthogonal to the inspection surface 28. The base of each of the support masts 34 is placed on one of the bearing tracks 30. In this configuration, the inspection system 42 is able to move across the bearing tracks 30, over the base with the inspection surface 28, to inspect each component 1 placed thereon.

The upper tier 38 comprises a horizontal beam attached to and supported by the support masts 34, and having fixturing to which the camera 40 is mounted. The exemplary camera 40 comprises a digital, monochrome line-scan camera, having eight kilobyte (8K) resolution, with a 175 millimeter lens attached, and preferably located a range of 150 millimeters to 450 millimeters from the surface of the inspected component 1. The camera 40 preferably provides a minimum pixel resolution of four kilobytes, and a maximum square pixel size of ten microns by ten microns. The camera 40 electrically signally interfaces to a first computer 50 in the workstation 10 using an image acquisition card, preferably a PCI- or PXI-based frame grabber card (not shown).

The lower tier 36 comprises a horizontal beam attached to and supported by the support masts 34, and having fixturing to which the lighting system 37 is mounted. The lighting system 37 includes a light source (not shown) emitted in the direction of the inspected surface 28. The light source preferably comprises red diffuse light generated using an array of red light-emitting diodes ('LED'). Light emanating from the array of red LEDs is preferably passed through a corresponding array of fresnel lens to diffuse the light source projected onto the inspected component 1. The light system is preferably located so the emanating light is not directly orthogonal to the surface of the component, with the object being to create a visually discernible difference between a surface pore and the machined surface. Red light is preferably used when the inspected surface is machined aluminum, although other colors of the spectrum may be used when other metal material is to be inspected. The lighting system 37 includes a scanning slit 39 placed perpendicular to axis 27, and providing an opening at least the width of the component 1 positioned for inspection. Axis 27 defines a Y-dimension, and an X-dimension is defined to be orthogonal to the Y-dimension in a plane defined by inspected surface 28, thus defining an XY coordinate system, which is discussed hereinafter. The upper tier 38 is preferably located above lower tier 36 in a manner to permit the camera 40 to capture an image of a portion of the inspected surface of the component 1 when it is positioned for inspection. The camera 40 is preferably positioned to capture an image of the component through the scanning slit 39 in the lighting system 37.

The exemplary workstation 10 comprises a rack-mountable stack including five computers 50, 51, 52, 53, 54, each said computer preferably having a single microprocessor device, each operable to function independently and concurrently. All five computers are mounted in a single cabinet or rack, and appropriately interconnected to accept input data from the camera 40, analyze the input data, render a decision on acceptability of the machined surface of the specific component being inspected, provide and store detailed statistical analysis of the input data for each component, and advance each component through the inspection station 14, either directly or through interaction with an operator. Computer 50 acquires input data from the camera 40 in form of a digital image of the machined surface of the component 1, as previously described; Computers 51, 52, and 53 process the image to a scaled image, analyze and invert the scaled image, and compare the image to a known, expected image of the surface, further analyze the scaled image and compare it to the inverted image to create a final image. Computer 54 performs statistical analysis on the final image, outputs the statistical analysis results to one or mores screens for operator review, and provides coordination of graphical user interfaces ('GUI'), the output of which includes viewing and workstation monitors. The GUIs are developed to meet the specific need of the individual application and the operators and engineers, as known to one skilled in the art, and not discussed in detail herein. The various systems and components are electrically connected using appropriately sized and shielded cables which conform to industry standards applicable to a manufacturing facility.

Computer 50 is signally electrically connected to an output of the line-scan camera 40. The camera 40 is operable to acquire an original, two-dimensional (in XY coordinates), digital, monochrome image of the machined surface of interest on the component 1, and communicate the image to computer 50. The original digital monochrome image comprises a series of pixels, each comprising a digitized representation of a portion of the machined surface of interest, and preferably having eight-bit grayscale resolution, i.e. ranging in value from 0 (black) to 255 (white), each pixel a square sized in the range of ten microns by ten microns.

Figure 5:
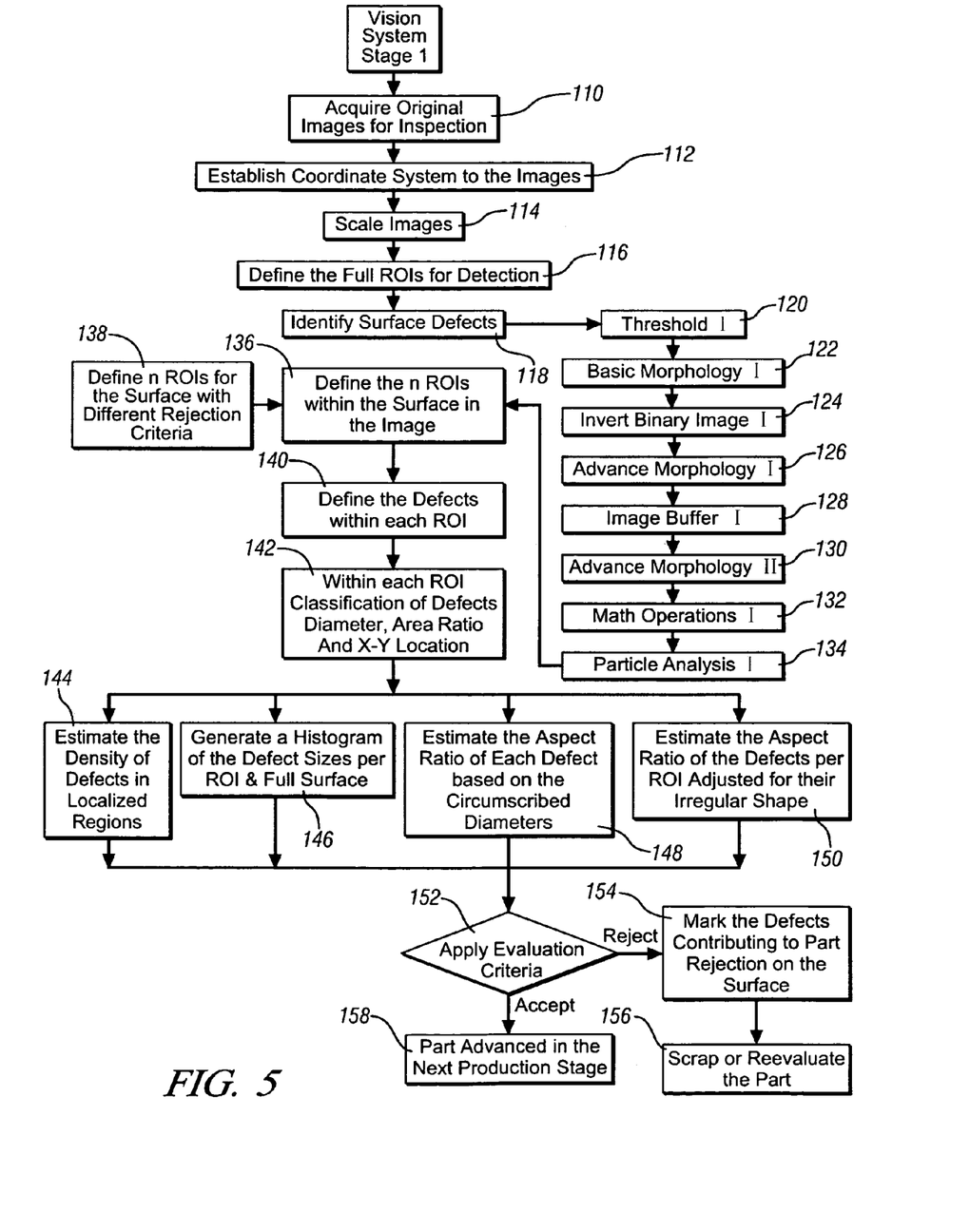
FIG. 5 is a diagram of a first flowchart for evaluating a surface, in accordance with the present invention; and, FIG. 6 is a diagram of a second flowchart for evaluating a surface, in accordance with the present invention.

Referring now to FIG. 5, a method to use a vision system to capture an image of the machined surface of the cast-metal component, to evaluate the image to identify and separate surface defects from design features, is described in detail. The method is preferably executed as one or more algorithms contained in one of the computers of the workstation 10. A skilled practitioner is generally able to design, develop, implement, and execute algorithms for application in a computer, in conjunction with external devices such as those described with reference to FIGS. 1-4, and this process is not described in detail herein.

The method includes capturing and processing a digital image representative of the machine surface of component 1, using the aforementioned vision system described with reference to FIGS. 1-4. This includes first acquiring the original pixelated image of the machined surface (Block 110), wherein each pixel comprises a digitized representation of a portion of the machined surface, as described hereinabove. The inspection station 42 moves along the pair of bearing tracks 30, parallel to the Y-axis, at a predetermined rate, with the lighting system 37 illuminating the surface of the inspected component 1. The camera 40 digitally captures a series of line-scan images of the component, each one pixel in length. When a complete original digital image of the machined surface of the component 1 is acquired, it is oriented and scaled to the aforementioned XY coordinate system, and has units of measure, preferably in millimeters, representative of the actual component being inspected (blocks 112, 114). The orientation and scaling is accomplished by employing pattern recognition methods combined with known design features of the machined surface. The known design features, include, for example, cylinder bores and bolt holes when the component 1 comprises an engine block, and have been predetermined and preprogrammed into at least one of the computers 50, 51, 52, 53, 54 for use as an element of algorithm execution. A series of regions of interest are predetermined and preprogrammed into the computer for use during component analysis. Each region of interest comprises a specific area of the machine surface being inspected, with corresponding image captured by the vision system. Each region of interest has a unique threshold level assigned thereto, useable when identifying surface defects (Block 116).

A series of operations are executed to identify surface defects in the inspected surface (Block 118). The imaging algorithm, designated as Threshold I through Math Operations I, (blocks 120 through 132) describes the steps executed to process the acquired image and separate the particles, in a binary form, to identify porosity defects in the inspected surface. The first portion of this process includes generating an inverted digital image of the machined surface. This preferably comprises analyzing each pixel of the original pixelated image relative to a cluster of pixels contiguous thereto; resolving each analyzed pixel to be either one of a digital "1" or digital "0", based upon the analysis of the original pixelated image and the cluster of pixels contiguous thereto; and, inverting each resolved analyzed pixel, as described hereinbelow.

Referring again to FIG. 5, a threshold I step is executed (Block 120) wherein a clustering threshold operation is executed. The clustering threshold operation uses a statistical algorithm, comprised of known Gaussian analysis techniques, to convert each greyscale pixel to a digital zero value or a digital 255 value, thus resolving the acquired image into a binary image. A cluster of pixels contiguous to a specific pixel is analyzed. The value of the specific, centrally located pixel, is converted to either 0 (black) or 255 (white), based on the statistical analysis of the cluster. Each pixel in the acquired image is analyzed thusly.

A basic morphology I operation is executed (block 122), comprising an erosion function wherein small particles are filtered out of the acquired image, e.g. an individual pixel having a value of 255 surrounded by a large mass of pixels, each having a value of zero, is converted to a value of zero. This step is able to run several times during execution of the algorithm to clean the image and minimize the number of noisy objects in a specific region of interest, thus improving accuracy of the inspection process.

The image remaining after execution of the basic morphology I operation is inverted (block 124). This comprises changing each pixel value from zero to 255, or, alternatively, from 255 to zero. The result is an image that is digitally reversed from the input image, i.e. a digital equivalent of a photographic negative. The inverted image is stored in an image buffer, preferably in computer 52, for subsequent use (block 128).

In the advanced morphology step, a second image of the machined surface is generated, comprising eliminating the known design surface features from the inverted digital image (block 130). This comprises identifying the aforementioned known design features of the machine surface, using information stored in the computer 54. Identifiable large objects and border objects are removed, whereas known cavities, comprising, e.g. valve seats, guides, and holes, are 'filled in' in the image data file. Known edges are smoothed.

The math operation step (block 132) comprises comparing each pixel of the inverted digital image with a correspondingly located pixel of the second image. Pixel location is based upon the pixelated image oriented and scaled to the XY coordinate system, as previously described. The result of this action is to identify any surface feature, i.e. pores and other defects, common to the inverted digital image and the second image. The math operation step preferably comprises comparing each pixel of the inverted digital image with the correspondingly located pixel of the second image by executing a simple digital logic operation referred to as an Exclusive-OR (XOR) function. The resultant image from this operation is analyzed for conformance to predetermined quality standards.

Statistical particle analysis is performed on the resultant image. (Block 134). This comprises identifying the regions of interest in the original pixelated image of the machined surface, relative to the scaled XY coordinate system for the digital image (Block 136). A high detection threshold is employed for evaluating pores and identifying defects when the region of interest comprises a critical region of interest, thus identifying relatively small surface pores, typically in the range of 0.3 millimeters, to be identified as defects. A low detection threshold is employed for evaluating surface pores and identifying defects when the region of interest comprises a non-critical region of interest, thus requiring a pore to be relatively large, typically in the range of 2.0 millimeters, before being identified as a defect (Block 138). A critical region of interest for a machined surface of a cast metal component typically includes any region subjected to high levels of mechanical stress or thermal stress in-use. Typical regions include cylinder walls and edges, and gasket squish areas, i.e. areas at which gaskets are compressed on a typical engine block when a cylinder head (not shown) is assembled thereto.

The defects are identified and classified within each region of interest, comprising identifying location and magnitude of each surface defect within each region of interest, relative to the scaled XY coordinate system for the digital image (Block 140). Magnitude of each surface defect is classified based upon several analysis techniques, including defect or pore diameter, defect or pore area ratio, and defect XY location. The pore diameter is preferably defined as a diameter of the smallest circle able to completely circumscribe the identified pore, or defect, and is measured in millimeters. Pore area ratio comprises a calculation of a ratio between area of the circle defined by the pore diameter, and actual area of the identified pore, based upon pixels. As part of analysis, a high detection threshold for pore size is typically in the range of 0.3 millimeters when in a critical region of interest. Therefore, any pore having a diameter in excess of 0.3 millimeters is considered an identifiable defect in a region of interest near a cylinder wall, or near a gasket squish area and edge. Alternatively, a low detection threshold for pore size is typically in the range of 2.0 millimeters when in a non-critical region of interest. Therefore any pore having a diameter in excess of 2.0 millimeters is considered an identifiable defect in a region of interest substantially away from a cylinder wall. Proximity of pores in each region of interest is important, and a typical threshold for minimum distance between pores is in the range of 3.0 millimeters (Block 142).

After defects have been identified and classified, they are analyzed by the computer 54. An estimate of defect density is calculated for each region of interest (Block 144). A histogram is generated (Block 146), comprising a showing of quantity of defects by size for each region of interest and for the entire machined surface of the component. Other analyses are conducted involving estimating area ratio for each identified defect (block 148), and estimating area ratios of defects of each region of interest, adjusted for irregular shapes (block 150).

The defects are statistically analyzed and evaluation criteria are applied, and a decision is made whether to reject or accept the component being inspected (block 152). Statistical analysis is preferably provided using readily available software packages, known to a skilled practitioner, and not described in detail herein. The defects leading to rejection of a given part are physically marked on the part (block 154), and it is either scrapped or used in further analysis (block 156), as determinable by quality procedures in the manufacturing plant. The accepted parts are conveyed down the manufacturing line for further processing and assembly (block 158).

Figure 6:
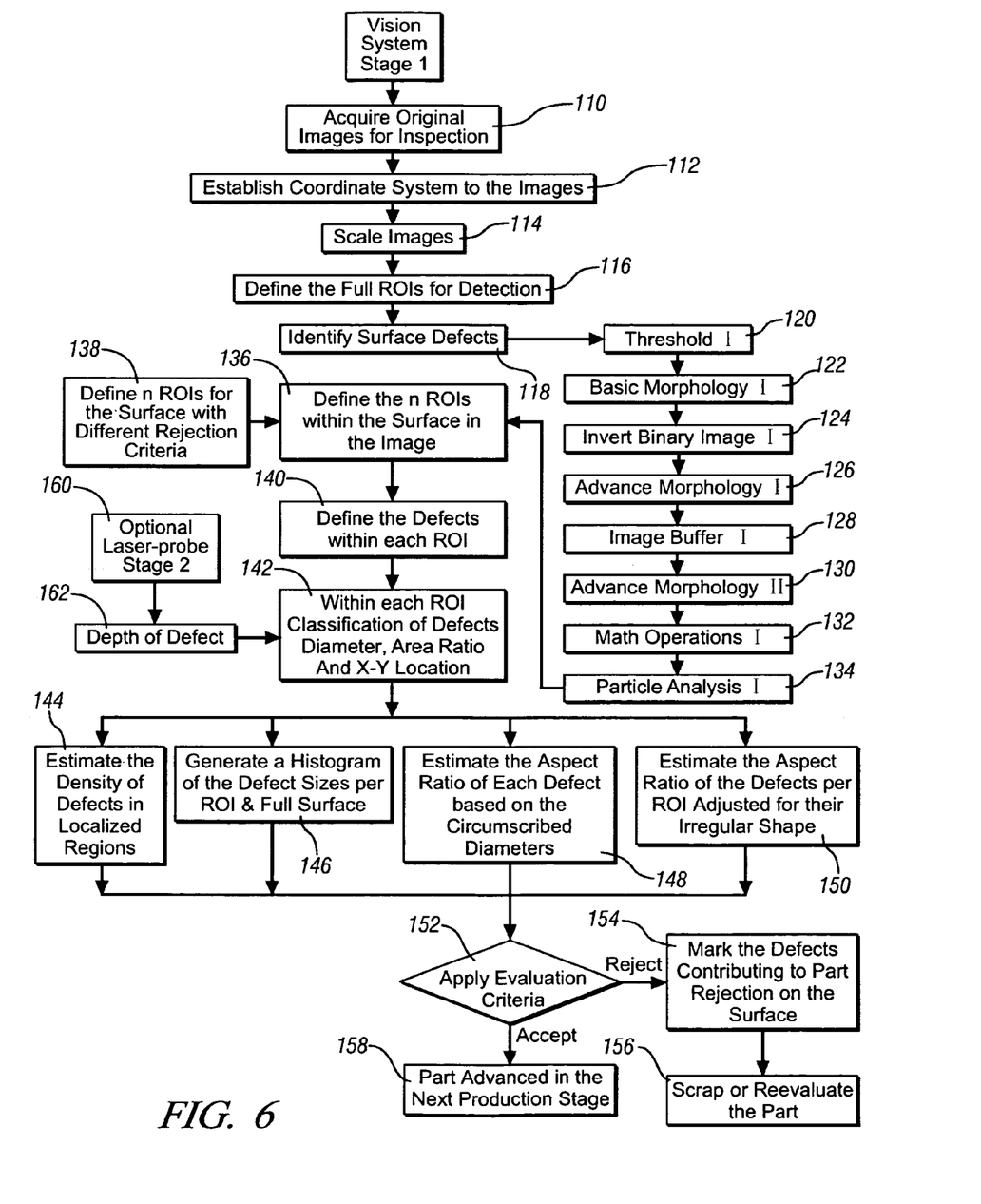

Referring now to FIG. 6, a second system and method to evaluate the machined surface of a cast-metal component, to identify and separate surface defects from design features, is described in detail. The hardware referred to with regard to FIG. 1-4 is unchanged, and a laser probe (not shown) is added to the two-tiered camera/lighting scanning mast arrangement of inspection station 42 and signally connected to the workstation 10 for processing of the signal. The laser probe is operable to detect a depth of each detected surface defect. The method, as shown in FIG. 6, is in essence equivalent to the method detailed with regard to FIG. 5, with steps 160, 162 added. The depth dimension, in the Z-dimension orthogonal to the XY-coordinate system, is input into the analysis as an added element to the classification of defects (blocks 162, 142). The evaluation criteria (block 152) determining whether to accept or reject a specific component may be adjusted, and this evaluation and decision making is determinable by a skilled practitioner.

The invention has been described with specific reference to the embodiments and modifications thereto. This includes any embodiment wherein the inspected component is moved under the camera, and alternative methods of acquiring the original image, e.g. using a multidimensional digital camera. Further modifications and alterations may occur to others upon reading and understanding the specification. It is intended to include all such modifications and alterations insofar as they come within the scope of the invention.

The invention claimed is:

1. Method to operate a vision system to evaluate a machined surface of a cast-metal component, comprising:
    acquiring from the vision system an original pixelated image of the machined surface, wherein each pixel comprises a digitized representation of a portion of the machined surface;
    identifying known design surface features in the original pixelated image, based upon predetermined criteria;
    orienting and scaling the original pixelated image of the machined surface to an XY coordinate system, based upon the known design surface features;
    generating an inverted digital image of the machined surface;
    generating a comparison image of the machined surface, comprising eliminating the known design surface features from the inverted digital image;
    comparing each pixel of the inverted digital image with a correspondingly located pixel of the comparison image, said location based upon the pixelated image oriented and scaled to the XY coordinate system;
    identifying any surface feature common to the inverted digital image and the comparison image;
    analyzing statistically each identified surface feature common to both images for conformance to a threshold; and,
    identifying a defect as any identified surface feature common to both images which exceeds the threshold.

2. The method of claim 1, wherein generating an inverted digital image of the machined surface, comprises:
    analyzing each pixel of the original pixelated image relative to a cluster of pixels contiguous thereto;
    resolving each analyzed pixel to be either one of a digital "1" or "0", based upon the analysis of the original pixelated image and the cluster of pixels contiguous thereto; and,
    inverting each resolved analyzed pixel.

3. The method of claim 1, wherein comparing each pixel of the inverted digital image with the correspondingly located pixel of the comparison image, comprises executing a logic exclusive-or function on each pixel of the inverted digital image with the correspondingly located pixel of the comparison image.

4. The method of claim 1, wherein analyzing statistically the identified surface features common to both images for conformance to a threshold comprises:
    identifying a plurality of regions of interest in the original pixelated image of the machined surface, wherein each region of interest comprises a predetermined area on the machined surface, relative to the scaled XY coordinate system for the digital image;
    selecting the threshold to be a high detection threshold, when the region of interest comprises a critical region of interest; and,
    selecting the threshold to be a low detection threshold, when the region of interest comprises a non-critical region of interest.

5. The method of claim 4, wherein a critical region of interest comprises an area of the machine surface exposed to high levels of mechanical force or thermal energy during use of the component.

6. The method of claim 5, further comprising:
    identifying a plurality of regions of interest in the original pixelated image of the machined surface, wherein each region of interest comprises a predetermined area on the machined surface, relative to the scaled XY coordinate system for the digital image; and,
    identifying a location and magnitude of each surface defect within each region of interest.

7. The method of claim 6, further comprising calculating a density of surface defects within each specified region of interest.

8. Method to operate a vision system to evaluate a machined surface of a cast-metal component, comprising:
    acquiring from the vision system an original pixelated image of the machined surface, wherein each pixel comprises a digitized representation of a portion of the machined surface;
    identifying known design surface features in the original pixelated image, based upon predetermined criteria;
    orienting and scaling the original pixelated image of the machined surface to an XY coordinate system, based upon the known design surface features;
    generating an inverted digital image of the machined surface;
    generating a comparison image of the machined surface, comprising eliminating the known design surface features from the inverted digital image;
    comparing each pixel of the inverted digital image with a correspondingly located pixel of the comparison image, said location based upon the pixelated image oriented and scaled to the XY coordinate system;
    identifying any surface feature common to the inverted digital image and the comparison image;
    analyzing statistically each identified surface feature common to both images for conformance to a threshold, comprising:
        a. identifying a plurality of regions of interest in the original pixelated image of the machined surface, wherein each region of interest comprises a predetermined area on the machined surface, relative to the scaled XY coordinate system for the digital image;
        b. selecting the threshold to be a high detection threshold, when the region of interest comprises a critical region of interest, wherein the critical region of interest comprises an area of the machine surface exposed to high levels of mechanical force or thermal energy during use of the component;
        c. selecting the threshold to be a low detection threshold, when the region of interest comprises a non-critical region of interest;
    identifying a defect as any identified surface feature common to both images which exceeds the threshold;
    identifying a location and magnitude of each surface defect within each region of interest;
    calculating a density of surface defects within each specified region of interest; and,
    analyzing each defect in relationship to neighboring defects, and in relationship to sharp or tight cornered features on the component.

9. The method of claim 1, wherein acquiring an original pixelated image of the machined surface comprises: acquiring a monochrome digitized representation of a portion of the machined surface.

10. The method of claim 1, further comprising:
    controlling a plurality of conveyors to move the cast-metal component into position for further processing when a quantity of identified defects is below a threshold, and, controlling the plurality of conveyors to move the cast-metal component out of the position for further processing when the quantity of identified defects exceeds the threshold.

11. The method of claim 10, further comprising: marking physically on each rejected component at least one of the defects leading to rejection.

12. Method to operate a vision system to evaluate a machined surface of a cast-metal component, comprising:
   a) acquiring from the vision system an original pixelated image of the machined surface;
   b) identifying known design surface features in the original pixelated image;
   c) orienting and scaling the original pixelated image of the machined surface to an XY coordinate system, based upon the known design surface features;
   d) generating an inverted digital image of the machined surface;
   e) generating a comparison image of the machined surface, comprising eliminating the known design surface features from the inverted digital image;
   f) comparing each pixel of the inverted digital image with a correspondingly located pixel of the comparison image;
   g) identifying any surface feature common to the inverted digital image and the comparison image;
   h) analyzing each identified surface feature common to both images; and,
   i) identifying a defect as any identified surface feature common to both images which exceeds a threshold.

13. System for evaluating a machined surface of a cast-metal component, comprising:
   a plurality of conveyors, operable to move the cast-metal component to and from a porosity inspection station, the porosity inspection station comprising: a digital monochrome camera, a lighting station, and a precision-controlled transfer station; a computer workstation: having a plurality of data processing computers, and a graphical user interface; operably connected to the plurality of conveyors, and signally and operably connected to the porosity inspection station;
   the system operable to:
   a) acquire an original pixelated image of the machined surface, wherein each pixel comprises a digitized representation of a portion of the machined surface;
   b) identify known design surface features in the original pixelated image, based upon predetermined criteria;
   c) orient and scale the original pixelated image of the machined surface to an XY-coordinate system, based upon the known design surface features;
   d) generate an inverted digital image of the machined surface;
   e) generate a comparison image of the machined surface, which comprises eliminating the known design surface features from the inverted digital image;
   f) compare each pixel of the inverted digital image with a correspondingly located pixel of the comparison image, said location based upon the pixelated image oriented and scaled to the XY-coordinate system;
   g) identify any surface feature common to the inverted digital image and the comparison image;
   h) analyze statistically each identified surface feature common to both images for conformance to a threshold; and,
   i) identify a defect as any identified surface feature common to both images which exceeds the threshold.

14. The system of claim 13, further comprising:
   the computer workstation operable to control the plurality of conveyors to move the cast-metal component into position for further processing when a quantity of identified defects is below a threshold, and, control the plurality of conveyors to move the cast-metal component out of the position for further processing when the quantity of identified defects exceeds the threshold.

15. The system of claim 14, wherein the system is operable to function at a manufacturing production rate.

16. The system of claim 15, wherein the manufacturing production rate comprises analyzing and moving each cast-metal component within a time interval substantially close to twenty seconds.

17. The system of claim 13, wherein the porosity inspection station, comprising: a digital monochrome camera, a lighting station, and a precision-controlled transfer station further comprises a laser probe is operable to detect a depth of each detected surface defect.

* * * * *